United States Patent [19]
Feuerstein et al.

[11] Patent Number: 5,994,529
[45] Date of Patent: Nov. 30, 1999

[54] GLIOMA-ASSOCIATED NUCLEIC ACID PROBES

[75] Inventors: Burt G. Feuerstein; Gayatry Mohapatra; Dong Hyung Kim, all of San Francisco, Calif.

[73] Assignee: The Regents of the University of California, Oakland, Calif.

[21] Appl. No.: 08/812,609

[22] Filed: Mar. 6, 1997

Related U.S. Application Data

[63] Continuation of application No. 08/403,457, Mar. 14, 1995, Pat. No. 5,635,351.

[51] Int. Cl.$^6$ .................................................. C07H 21/04
[52] U.S. Cl. ...................................... 536/24.31; 536/23.5
[58] Field of Search ........................ 435/810; 536/24.31, 536/23.5

[56] References Cited

U.S. PATENT DOCUMENTS

| | | | |
|---|---|---|---|
| 4,837,306 | 6/1989 | Ling et al. | 530/387 |
| 4,923,807 | 5/1990 | Webb et al. | 435/69.2 |
| 4,933,294 | 6/1990 | Waterfield et al. | 436/501 |
| 4,980,461 | 12/1990 | Litt | 536/27 |
| 5,075,217 | 12/1991 | Weber | 435/6 |
| 5,098,823 | 3/1992 | Bodmer et al. | 435/6 |
| 5,110,906 | 5/1992 | Maddon et al. | 530/350 |
| 5,132,212 | 7/1992 | Kirsch et al. | 435/69.4 |
| 5,183,884 | 2/1993 | Kraus et al. | 536/23.5 |
| 5,212,290 | 5/1993 | Vogelstein et al. | 530/387.7 |
| 5,219,726 | 6/1993 | Evans | 435/6 |
| 5,239,060 | 8/1993 | Kunkel et al. | 530/350 |
| 5,306,616 | 4/1994 | Lupski et al. | 435/6 |
| 5,350,840 | 9/1994 | Call et al. | 536/23.1 |
| 5,364,759 | 11/1994 | Caskey et al. | 435/6 |
| 5,366,889 | 11/1994 | MacDonald et al. | 435/252.3 |
| 5,369,004 | 11/1994 | Polymeropoulos et al. | 435/6 |
| 5,385,915 | 1/1995 | Buxbaum et al. | 514/313 |
| 5,395,767 | 3/1995 | Murnane et al. | 435/320.1 |
| 5,401,835 | 3/1995 | Chishti | 536/23.2 |
| 5,427,932 | 6/1995 | Weier et al. | 435/91.2 |
| 5,487,970 | 1/1996 | Rowley et al. | 435/6 |
| 5,529,925 | 6/1996 | Morris et al. | 435/252.3 |
| 5,538,846 | 7/1996 | Meeker | 435/6 |
| 5,556,955 | 9/1996 | Vergnaud | 536/24.31 |
| 5,578,450 | 11/1996 | Thibodeau et al. | 435/6 |
| 5,622,851 | 4/1997 | Maley et al. | 435/227 |
| 5,658,730 | 8/1997 | McGill et al. | 435/6 |
| 5,665,549 | 9/1997 | Pinkel et al. | 435/6 |
| 5,670,314 | 9/1997 | Christman et al. | 435/6 |
| 5,686,288 | 11/1997 | MacDonald et al. | 435/325 |
| 5,756,696 | 5/1998 | Gray et al. | 536/23.1 |

OTHER PUBLICATIONS

Gilbert et al., J. Natl. Cancer Inst. 67(2), 301–306 (1981).
Motegi et al., J. Med. Genet. 25(9), 628–630 (1988).
Filatov et al., Mol. Biol. Rep. 12(2), 117–122 (1987).
Hecht et al., Cancer Genet. Cytogenet. 14(3–4), 197–203 (1985).
Fidzianska et al., Probl. Med. Wieku Rzwoj. 16, 163–165 (1990).
Wilmoth et al., Cancer Genet. Cytogenet. 15(1–2), 95–98 (1985).
Sutherland, Am. J. Hum. Genet. 31(2), 136–148 (1979).
Muller et al., Hum. Genet. 60(3), 274–275 (1982).
Hoo et al., Ann. Genet. 25(4), 249–252 (1982).
Casals et al., Nucleic Acids Res. 18(10), 3108 (1990).
Stenman et al., Cytogen. Cell Genet. 60(3–4), 206–207 (1992)(abstract only).
Kennerknecht et al., Hum. Genet. 86(2), 238–240 (1990)(abstract only).
Bello et al., Int. J. Cancer, 57 172–175 (Apr. 15, 1994).
Chung et al., Genes Chromosom. Cancer, 3(5), 323–331 (1991) Abstract Only.
Collins, Int. Rev. Exp. Pathol. 24:135–202 (1983).
Dutrillaux, et al., Cancer Genet. Cytogenet., 49: 203–217 (1990).
Fischer et al., Eur. J. Cancer, 30A(8), 1124–1127 (Aug. 1994).
Fults, et al., Genomics, 14, 789–801 (1992).
Kallioniemi et al., PNAS, 91:2156–2160 (1994).
Kallioniemi et al. Science 258: 818–821 (1992).
Kumabe et al., Oncogene, 7, 627–633 (1992).
Mikkelsen et al. J. Cellular Biochm. 46:3–8 (1991).
Oberstrass et al., Verh. Dtsch. Ges. Pathol., 78–413–417 (1994).
Rasheed et al., Genes Chromosom. Cancer, 5(1), 75–82 (1992) Abstract Only.
Roberts et al., Cancer Res., 49, 5407–5413 (1989).
Rutka, Acta. Neuropathol. (Berl) 75:92–103 (1987).
Sato, et al., Cancer. Res., 50: 7184–7189 (1990).
Schlegel et al., Verh. Dtsch. Ges. Pathol., 78, 204–207.
Silverberg et al. CA Cancer J. Clin. 40: 9–26 (1990).
Smith, et al., Breast Cancer Res. Treat., 18: Suppl. S51–S54 (1991).
Trent, et al., PNAS 83:470–473 (1986).
van Deimling et al., Int. J. Cancer, 57, 676–680 (Jun. 1, 1994).
van de Vijver & Nusse, Biochim. Biophys. Acta. 1072: 33–50 (1991).
Vogeley et al., Pathol. Res. Pract., 190(3), 262 (Abstract 1994).
Welter et al., Cancer Lett., 52(1), 57–62 (1990) Abstract Only.
Olopade et al., Cancer Res., 52 2523–2529 (1992).

*Primary Examiner*—Kenneth R. Horlick
*Attorney, Agent, or Firm*—Majestic, Parsons, Siebert & Hsue, P.C.

[57] ABSTRACT

The present invention provides chromosomal amplifications and deletions associated with neoplastic growth of gliomas. These amplifications and deletions may be used for detecting and grading gliomas. The invention also provides compositions for the detection of gliomas.

25 Claims, No Drawings

GLIOMA-ASSOCIATED NUCLEIC ACID PROBES

This is a Continuation of application Ser. No. 08/403,457 filed Mar. 14, 1995, U.S. Pat. No. 5,635,351 the disclosure of which is incorporated herein by reference for all purposes.

This invention was made with Government support under Grant No. CA-13525 and CA-61147 awarded by the National Institutes of Health. The Government has certain rights in this invention.

FIELD OF THE INVENTION

This invention pertains to the field of oncology. In particular this invention pertains to the identification of genomic amplifications and deletions associated with gliomas.

BACKGROUND OF THE INVENTION

Many cancers are believed to result from a series of genetic alterations leading to progressive disordering of normal cellular growth mechanisms (Nowell, *Science* 194:23 (1976), Foulds, *J. Chronic Dis.* 8:2 (1958)). In particular, the deletion or multiplication of copies of whole chromosomes or chromosomal segments, and higher level amplifications of specific regions of the genome are common. See, for example, Smith, et al., *Breast Cancer Res. Treat.*, 18: Suppl. 1: 5–14 (1991), van de Vijer & Nusse, *Biochim. Biophys. Acta.* 1072: 33–50 (1991), Sato, et al., *Cancer. Res.*, 50: 7184–7189 (1990). In fact, the amplification and deletion of DNA sequences containing proto-oncogenes and tumor-suppressor genes, respectively, are frequently characteristic of tumorigenesis. Dutrillaux, et al., *Cancer Genet. Cytogenet.*, 49: 203–217 (1990).

In particular, losses and gains of genetic material have been associated with glioma progression (Mikkelson et al. *J. Cellular Biochm.* 46:3–8 (1991)). In particular, it is believed gains and losses of genetic material serve as signposts for oncogenes and tumor suppressor genes in gliomas. Although gliomas are the most common primary neoplasms of the central nervous system, only modest progress has been made in diagnosing and treating malignant gliomas (Silverberg et al. *CA Cancer J. Clin.* 40: 9–26 (1990)). The identification of the genetic events leading to neoplastic transformation and subsequent progression aid in elucidating the biological basis for disease, permit early tumor detection and prediction of therapeutic response thereby improving the disease prognosis.

Cytogenetics is the traditional method for detecting amplified or deleted chromosomal regions. The resolution of cytogenetic techniques is limited, however, to regions larger than approximately 10 Mb (approximately the width of a band in Giemsa-stained chromosomes) because of the complex packing of DNA into the chromosomes. In complex karyotypes with multiple translocations and other genetic changes, traditional cytogenetic analysis is of little utility because karyotype information is lacking or cannot be interpreted. Teyssier, *Cancer Genet. Cytogenet.*, 37: 103 (1989). Furthermore conventional cytogenetic banding analysis is time consuming, labor intensive, and frequently difficult or impossible.

Recent methods assessing the amount of a given DNA sequence in a chromosome are more sensitive than the traditional cytogenetic techniques. These methods employ cloned DNA or RNA probes that are hybridized to chromosomal DNA. This method is effective even if the genome is heavily rearranged so as to eliminate useful karyotype information. However, this Southern blotting method gives only a rough estimate of the copy number of a DNA sequence, and does not provide any information about the localization of that sequence within the chromosome.

Comparative genomic hybridization (CGH) is a more recent approach to identify the presence and localization of amplified or deleted sequences (See, e.g., Kallioniemi et al. *Science* 258: 818–821 (1992)). CGH, like Southern blotting, reveals amplifications and deletions irrespective of genome rearrangement. It produces a map of relative DNA copy number as a function of chromosomal location by comparing the hybridization efficiency of tumor and reference DNA to metaphase chromosomes. CGH, however, has advantages over Southern blotting, providing a more quantitative estimate of copy number, and also providing the location of amplified or deleted sequences in the normal chromosome. Where a deletion or amplification is limited to the loss or gain of one copy of a sequence, the CGH resolution is usually about 5–10 Mb.

Unfortunately, the sensitivity of both CGH and Southern blotting techniques to contamination of tumor samples by normal cells makes estimating the copy number of particular chromosomal sequences within the tumor cell population very difficult. In addition, another problem with conventional CGH is the presence of artifacts due to differential binding of digoxigenin- and biotin-labeled probes at specific chromosomal regions.

SUMMARY OF THE INVENTION

The present invention provides for novel genomic amplifications and deletions associated with the neoplastic transformation and growth of glial cells. The particular glioma-associated amplifications include the following chromosomal regions: (1)(q21–23), (1)(q32), (1)(p36-pter), (1)(p33–34.1), (1)(p34.2–34.3), (3)(q27–28), (4)(p16), (4)(q26–27), (5)(p12–13), (5)(q31.2), (7)(p22), (7)(q22), (7)(q34–36), (10)(q22), (10)(q26),(11)(q13), (11)(q14–21), (11)(q23), (11)(p11.2–12) (12)(p13.3), (12)(p11.2–12.2), (12)(q13–14), (14)(q11.2–13), (14)(q22–23), (14)(q31-qter), (15)(q13), (15)(q15), (17)(q24–25), (17)(p11.2–12), (19)(q13), (19)(q13.4), (20)(p11.2), (20)(q13), (X)(p22), (X)(q27–28), and (Y)(p11.2–11.3). Particular glioma-associated deletions include the following chromosomal regions: (2)(p23–25), (4)(q31.3–35), (5)(q34–35), (6)(q23–27), (8)(q23–24.1), (9)(p23–24), (11)(p15), (11)(q21–25), (12)(q21–22), (13)(q31–32), (14)(q23–32), and (21)(q21–22.1). Of these glioma-associated deletions and amplifications, (6)(q23–27), (13)(q31–32), and (14)(q23–32) are particularly preferred deletions, while (14)(q11.2–13), (14)(q22–23) and (14)(q31-qter) are particularly preferred amplifications.

The above-identified amplifications and deletions may be used as markers to detect neoplastic growth of glial cells. Thus, in one embodiment, this invention provides for a method of detecting glioma cells. The method involves providing a nucleic acid sample and detecting in the sample one or more of the above-identified amplifications or a deletions. More preferably the method involves detecting at least three of the above identified amplifications or deletions.

The amplifications and deletions may be detected by any of a number of methods well known to those of skill in the art. Preferred methods involve detecting nucleic acid sequences within the above-identified glioma-associated amplifications and deletions. Particularly preferred sequences include sequences corresponding to individual promoters, genes, or open reading frames of nucleic acids within the above-identified deletions and amplifications.

Preferred methods of detection involve hybridization of a nucleic acid probe with a nucleic acid found in the deletions or amplifications. In one preferred embodiment, the detection of the above-identified amplifications or deletions is hybridization (e.g. Southern or Northern blots) of a specific probe to a nucleic acid sample extracted from a one or more cells that are to be tested.

In another preferred embodiment, the detection of the above-by fluorescent in situ hybridization (FISH).

In yet another embodiment, the detection of the above-identified amplifications or deletions is by comparative genomic hybridization (CGH). More preferably, the CGH utilizes a sample nucleic acid from cells thought to comprise a glioma. Thus the comparative genomic hybridization may involve contacting normal metaphase chromosomes with a control nucleic acid consisting essentially of labeled total genomic DNA from healthy cells and a test nucleic acid comprising total genomic DNA from glioma cells. The method may further comprise determining the ratio of binding of the test probe to the reference probe. The probes are differently labeled so that they may be distinguished. Probes bearing flourescent labels are preferred with direct-labeled probes being most preferred.

In still yet another preferred embodiment, the glioma-associated amplifications and deletions may be detected by amplification methods. These methods preferably involve amplification (e.g. via PCR, LCR, self-sustained sequence replication, and the like) of nucleic acid sequences that occur within the above-identified amplifications and deletions. Particularly preferred nucleic acid sequences include genes and open reading frames. The amplification methods may also be used in conjunction with the other detection methods.

Where the method of detection comprises hybridization with a probe, a preferred probe specifically hybridizes under stringent conditions with a nucleic acid sequence found in a chromosomal region selected from the above-identified group of chromosomal amplifications and deletions. The detection method may preferably comprise hybridization with a probe where the probe has greater than about 95%, more preferably greater than about 98%, and most preferably greater than about 99% sequence identity with a nucleic acid sequence found in any of the above-identified chromosomal regions. In a particularly preferred embodiment, the probe comprises a nucleic acid sequence found in any of the above-identified chromosomal regions and is most preferably a promoter, a gene, or an open reading frame of a nucleic acid sequence found in any of the above-identified chromosomal regions.

In another embodiment, this invention provides for one or more of the probes described above.

This invention additionally provides for kits for the detection glioma cells. The kits include any of the probes described above. The kits may also include instructional materials describing how to use the kit contents in detecting amplifications or deletions associated with gliomas. In addition the kits may include one or more of the following: normal metaphase chromosomes, various labels or labeling agents to facilitate the detection of the probes, reagents for the hybridization including buffers, human Cot-1 DNA, bovine serum albumin (BSA) and other blocking agents, sampling devices including fine needles, swabs, aspirators and the like, positive and negative hybridization controls and so forth.

Definitions

A "nucleic acid sample" as used herein refers to nucleic acids obtained from one or more cells that are to be tested for the presence or absence of glioma-associated deletions or amplifications. The nucleic acid may be total genomic DNA, total mRNA, genomic DNA or mRNA from particular chromosomes, or selected sequences (e.g. particular promoters, genes, amplification or restriction fragments, cDNA, etc.) within particular glioma-associated amplifications or deletions. The nucleic acid sample may be extracted from particular cells or tissues. The tissue sample from which the nucleic acid sample is prepared is typically taken from a patient suspected of having the disease associated with the amplification or deletion being detected. Often the tissue sample will be a sample of a tissue suspected of being a glioma. The sample may be prepared such that individual nucleic acids remain substantially intact and typically comprises interphase nuclei prepared according to standard techniques. A "nucleic acid sample" as used herein may also refer to a substantially intact condensed chromosome (e.g. a metaphase chromosome). Such a condensed chromosome is suitable for use as a hybridization target in in situ hybridization techniques (e.g. FISH). The particular usage of the term "nucleic acid sample" (whether as extracted nuceic acid or intact metaphase chromosome) will be readily apparent to one of skill in the art from the context in which the term is used.

A "nucleic acid" or a "polynucleotide" refers to a deoxyribonucleotide or ribonucleotide polymer in either single- or double-stranded form, and unless otherwise limited, would encompass known analogs of natural nucleotides that can function in a similar manner as naturally occurring nucleotides.

"Hybridizing" refers the binding of two single stranded nucleic acids via complementary base pairing.

As used herein a "probe" is defined as a polynucleotide (either RNA or DNA) capable of binding to a complementary target cellular genetic sequence through one or more types of chemical bonds, usually through hydrogen bond formation. It will be understood by one of skill in the art that probes will typically substantially bind target sequences lacking complete complementarity with the probe sequence depending upon the stringency of the hybridization conditions. Thus substantial binding embraces minor mismatches that can be accommodated by reducing the stringency of the hybridization media to achieve the desired detection of the target polynucleotide sequence. The probes are preferably directly labelled as with isotopes or fluorescent labels, or indirectly labeled such as with biotin or an antigen to which a streptavidin complex or a labeled antibody may later bind. By assaying for the presence or absence of the probe, one can detect the presence or absence of the target. Nucleic acid probes can be prepared by a variety of methods known to those of skill in the art.

A "composition consisting essentially of one or more probes each of which hybridize specifically to a target polynucleotide sequence" refers to a collection of one or more probes which hybridize specifically to a polynucleotide sequence through complementary base pairing. "Hybridizing specifically" or "binding specifically" refers to complementary binding between a probe and a target nucleic acid sequence such that the probe nucleic acid binds substantially to the target sequence and nowhere else in the target chromosome or genome and thereby allows the detection of the presence or absence of the target sequence. The "composition consisting essentially of one or more probes . . ." may contain other nucleic acids which do not materially affect the detection of the target sequence. Such additional nucleic acids may include reference probes specific to a sequence in the centromere in the chromosome.

One of skill will recognize that the precise sequence of the particular probes described herein can be modified to a certain degree to produce probes that are "substantially identical" to the disclosed probes, but retain the ability to bind substantially to the target sequences. Such modifications are specifically covered by reference to the individual probes herein. The term "substantial identity" of polynucleotide sequences means that a polynucleotide comprises a sequence that has at least 95% sequence identity, more preferably at least 98%, and most preferably at least 99% sequence identity with a reference sequence as calculated by the methods described below using standard parameters.

Two nucleic acid sequences are said to be "identical" if the sequence of nucleotides in the two sequences is the same when aligned for maximum correspondence as described below. The term "complementary to" is used herein to mean that the complementary sequence is identical to all or a portion of a reference polynucleotide sequence.

Sequence comparisons between two (or more) polynucleotides are typically performed by comparing sequences of the two sequences over a "comparison window" to identify and compare local regions of sequence similarity. A "comparison window", as used herein, refers to a segment of at least about 20 contiguous positions, usually about 50 to about 200, more usually about 100 to about 150 in which a sequence may be compared to a reference sequence of the same number of contiguous positions after the two sequences are optimally aligned.

Optimal alignment of sequences for comparison may be conducted by the local homology algorithm of Smith and Waterman *Adv. Appl. Math.* 2: 482 (1981), by the homology alignment algorithm of Needleman and Wunsch *J. Mol. Biol.* 48:443 (1970), by the search for similarity method of Pearson and Lipman *Proc. Natl. Acad. Sci.* (U.S.A.) 85: 2444 (1988), by computerized implementations of these algorithms.

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

Another indication that nucleotide sequences are substantially identical is if two molecules hybridize to the same sequence under stringent conditions. Stringent conditions are sequence dependent and will be different in different circumstances. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is at least about 0.02 molar at pH 7 and the temperature is at least about 60° C.

Amplifications and deletions are identified herein using standard nomenclature referring to DAPI banding. For example, a deletion is designated (1)(q21–23) refers to a deletion on chromosome 1 (the number in the first pair of brackets) that ranges from band 21 to 23 on the q arm of the chromosome. The p arm is the short arm, while the q arm is the long arm. The terms pter and qter refer to the termini of the p and q arms respectively. Nomenclature and standard banding patterns are described by Francke, *Cytogen. and Cell Gen.*, 65: 206–218 (1994), which is incorporated herein by reference.

DETAILED DESCRIPTION

Detection of Glioma Associated Amplifications and Deletions

The present invention provides for a number of genomic deletions and amplifications that are characteristic of gliomas (see Table 1). A glioma, as used herein, is a glial cell that has undergone neoplastic transformation. Glial cells are typically non-conducting nerve cells including astrocytes, oligodendrocytes, Schwann cells, microglia and ependymal cells.

Individual deletions and amplifications, as well as patterns of deletion and amplification, may be used as diagnostic markers of gliomas. Patterns of deletion or amplification may also be used to classify various grades of neoplasia of glial cells (e.g. astrocytoma/grade II, anaplastic astrocytoma/grade III, and glioblastoma multiforme/grade IV). In addition, the deletions and amplifications identified herein may be used to distinguish between different glial tumor types (e.g. astrocytomas, oligodendrogliomas, etc.) that are difficult, or impossible, to distinguish histologically. This distinction may be critical to selection of a therapeutic regimen as certain types of glial tumors are resistant to particular therapeutic modalities (e.g. radiation as opposed to drugs), while others are not. Thus, use of the amplifications and deletions described herein to distinguish particular glial cell types will greatly aid the selection of therapeutic modalities and thereby dramatically improve the disease prognosis.

The various deletions and amplifications described herein are expected to contain genes (e.g. oncogenes or tumor suppressor genes) that are intimately involved in the regulation of cell growth and division. Thus, the amplifications and deletions identified herein, will prove useful in elucidation of the particular pathways involved in signaling, growth regulation and the onset of neoplasia. In addition, the genomic amplifications and deletions described herein characterize genetic instabilities that occur in other cell types besides glial cells. Thus, these instabilities may be utilized to diagnose or predict tumorigenesis in a wide variety of cell types.

In a preferred embodiment, this invention provides methods of detecting a glioma by detecting an amplification or a deletion associated with, or characteristic of, neoplastic growth of a glial cell. Methods of detecting the presence or absence of deletions or amplifications are well known to those of skill in the art and include, but are not limited to, hybridization (e.g., Southern or Northern blots) with probes that are specific to nucleic acid sequences (e.g. specific genes) within the deleted or amplified regions, various in situ hybridization methods including fluorescent in situ hybridization (FISH) and comparative genomic hybridization (CGH), detection or quantification of mRNA transcripts encoded by nucleic acid sequences within the deleted or amplified regions, detection of translated proteins encoded by the particular nucleic acids sequences, detection of single strand conformation polymorphisms (SSCPs), and direct detection using various nucleic acid amplification strategies such as polymerase chain reaction (PCR), ligase chain amplification (LCR), self-sustained sequence replication, and the like.

One of skill will appreciate that where the region is deleted on only one chromosome, a deletion may be detected as a loss of heterozygosity at a particular locus. Where the region is deleted on both copies of a chromosome, the deletion may be detected as the complete elimination of nucleic acid at a particular chromosomal locus. In either case, deletions will preferably be detected as a reduction in copy number at a particular chromosomal location, as compared to a healthy control. Conversely, amplifications may be detected as an increase in copy number as compared to healthy control.

TABLE 1

Deletions and amplifications associated with gliomas.

| Chromosome | Deletions | Amplifications |
|---|---|---|
| 1 |  | (q21–23), (q32), (p36–pter), (p33–34.1), (p34.2–34.3) |
| 2 | (p23–25) |  |
| 3 |  | (q27–28) |
| 4 | (q31.3–35) | (p16), (q26–27) |
| 5 | (q34–35) | (p12–13), (q31.2) |
| 6 | (q23–27) |  |
| 7 |  | (p22), (q22), (q34–36) |
| 8 | (q23–24.1) |  |
| 9 | (p23–24) |  |
| 10 |  | (q22), (q26) |
| 11 | (p15), (q21–25) | (q13), (q14–21), (q23), (p11.2–12) |
| 12 | (q21–22) | (p13.3), (p11.2–12.2), (q13–14) |
| 13 | (q31–32) |  |
| 14 | (q23–32) | (q11.2–13), (q22–23), (q31–qter) |
| 15 |  | (q13), (q15) |
| 17 |  | (q24–25), (p11.2–12) |
| 19 |  | (q13), (q13.4) |
| 20 |  | (p11.2), (q13) |
| 21 | (q21–22.1) |  |
| X |  | (p22), (q27–28) |
| Y |  | (p11.2–11.3) |

Detection of Glioma-Associated Deletions and Amplifications

Particularly preferred methods of detection of glioma-associated deletions and amplifications include Southern or Northern hybridizations, in situ hybridization, comparative genomic hybridization, and various amplification based methods.

Detection by Northern or Southern Hybridization

Detection of glioma-associated amplifications or deletions by Northern or Southern hybridization generally involves isolating a nucleic acid sample (DNA or an mRNA) from one or more cells that are to be tested. The sample is hybridized with probes that specifically bind to nucleic acid sequences present in one or more glioma-associated deletions or amplifications. Detection and quantification of the hybridization complex formed between the probe and the sample nucleic acid indicates the presence or amount of the deletion or amplification nucleic acid sequence.

More particularly, in Southern hybridizations, DNA is isolated from cells obtained from the test organism and digested into varying length fragments using a restriction endonuclease. The fragments are separated, e.g. by electrophoresis, typically transferred to a nylon or nitrocellulose membrane and then hybridized to a nucleic acid probe corresponding to a nucleic acid sequence within the amplification or deletion region it is desired to detect. Amplifications may be detected by quantifying the amount of bound probe relative to one or more control probes. Deletions will be detected by the lack of formation of a hybridization complex where both copies of the region are deleted or by reduced probe binding, corresponding to a reduced copy number, as compared to one or more control probes. In a Northern blot, an mRNA sample isolated from the test organism is probed in a manner similar to the Southern blot.

One of skill in the art will recognize that there are numerous variations of Northern and Southern probing methods. Thus, for example, selected regions of genomic DNA or RNA (e.g. DNA from individual chromosomes, genes, cDNA, etc.) rather than total genomic DNA or RNA may be screened with the particular nucleic acid probe. Selected nucleic acid sequences may be isolated by various means known to those of skill in the art. For example, DNA corresponding to a particular region within one or more deletions may be amplified using standard methods well known in the art. These include, but are not limited to, polymerase chain reaction (PCR) (Innis, et al., *PCR Protocols. A guide to Methods and Application.* Academic Press, Inc. San Diego, (1990) which is incorporated herein by reference), ligase chain reaction (LCR) (see Wu and Wallace, *Genomics,* 4: 560 (1989), Landegren, et al., *Science,* 241: 1077 (1988) and Barringer, et al., *Gene,* 89: 117 (1990) each of which is incorporated herein by reference), transcription amplification (Kwoh, et al., *Proc. Natl. Acad. Sci. USA,* 86: 1173 (1989) which is incorporated herein by reference), and self-sustained sequence replication (Guatelli, et al., *Proc. Nat. Acad. Sci. USA,* 87: 1874 (1990) which is incorporated herein by reference), each of which provides sufficient amplification so that the target sequence can be detected by nucleic acid hybridization to a probe.

Other variations include alternative labeling strategies. Thus the probe may be directly labeled with a detectable label such as a fluorescent marker, or alternatively it may be indirectly labeled with a moiety (e.g. biotin or dioxigenin) that is subsequently specifically bound with a second labeled moiety (e.g. labeled streptavidin or a labeled antibody). Alternatively, methods that amplify the probe to detectable levels can be used, such as Qβ-replicase amplification. See, for example, Kramer, et al. *Nature,* 339: 401 (1989), Lizardi, et al. *Bio/Technology,* 6: 1197 (1988), and Lomell, et al., *Clin. Chem.* 35: 1826 (1989) which are incorporated herein by reference.

One of skill will appreciate that it is not necessary to immobilize the sample nucleic acid on a membrane. Variations include immobilizing the probes rather than the sample nucleic acid. The probes may be immobilized in a variety of formats, for example in an affinity column, or on a glass substrate (e.g. as high density arrays of different probes) as described produced by Affymax Inc. (see, e.g., Fodor et al. *Science,* 251: 767–773 (1991) and U.S. Pat. No. 5,143,854).

These and other variations are well known to those of skill in the art. For detailed descriptions of various hybridization methods see, for example, Sambrook, et al., *Molecular Cloning: A Laboratory Manual,* 2nd Ed., Vols. 1–3, Cold Spring Harbor Laboratory (1989); *Methods in Enzymology, Vol. 152: Guide to Molecular Cloning Techniques,* Berger and Kimmel (eds.), San Diego: Academic Press, Inc. (1987); or *Current Protocols in Molecular Biology,* Ausubel, et al. (eds.), Greene Publishing and Wiley-Interscience, New York (1987), all of which are incorporated herein by reference.

Detection by In Situ Hybridization

Detection of glioma-associated amplifications or deletions by in situ hybridization generally involves providing a nucleic acid sample to be tested, typically either a metaphase spread or interphase nuclei, hybridizing the nucleic acid sample with one or more probes that specifically bind to nucleic acid sequences found within the glioma-associated deletion or amplification regions, and detecting or quantifying the hybridized probes. Methods of in situ hybridization are well known to those of skill in the art. Several guides to the techniques are available such as Gall et al. *Meth. Enzymol.,* 21:470–480 (1981) and Angerer et al. P. 43–65 In: *Genetic Engineering: Principles and Methods* Setlow and Hollaender, eds. Vol 7, Plenum Press, New York (1985), which are incorporated herein by reference.

Generally, in situ hybridization comprises the following major steps: (1) fixation of tissue or biological structure to analyzed; (2) prehybridization treatment of the biological structure to increase accessibility of target DNA, and to reduce nonspecific binding; (3) hybridization of the mixture of nucleic acids to the nucleic acid in the biological structure or tissue; (4) posthybridization washes to remove nucleic acid fragments not bound in the hybridization and (5) detection of the hybridized nucleic acid fragments. The reagent used in each of these steps and their conditions for use vary depending on the particular application.

Typically, the nucleic acid sample is prepared by depositing cells, either as single cell suspensions or as tissue preparation, on solid supports such as glass slides and fixed by choosing a fixative which provides the best spatial resolution of the cells and the optimal hybridization efficiency.

In some applications it is necessary to block the hybridization capacity of repetitive sequences. In this case, human genomic DNA is used as an agent to block such hybridization. The preferred size range is from about 200 bp to about 1000 bases, more preferably between about 400 to about 800 bp for double stranded, nick translated nucleic acids.

Standard in situ hybridization techniques are used to probe a given sample. Hybridization protocols for the particular applications disclosed here are described in detail below. Suitable protocols are described in Pinkel et al. *Proc. Natl. Acad. Sci. USA,* 85:9138–9142 (1988) and in EPO Pub. No. 430,402.

Typically, it is desirable to use a dual color fluorescent in situ hybridization procedure (FISH), in which two probes are utilized, each labelled by a different fluorescent dye. A test probe that hybridizes to the region of interest is labelled with one dye, and a control probe that hybridizes to a different region is labelled with a second dye. A nucleic acid that hybridizes to a stable portion of the chromosome of interest, such as the centromere region, is often most useful as the control probe. In this way, differences between efficiency of hybridization from sample to sample can be accounted for.

Detection by Comparative Genomic Hybridization

It is also possible to detect the glioma-associated regions of amplification and deletion disclosed herein using comparative genomic hybridization. In comparative genomic hybridization, a nucleic acid sample isolated from one or more test cells is hybridized to normal chromosomes in a metaphase spread. A nucleic acid control from healthy cells is simultaneously hybridized to the same normal metaphase spread. The nucleic acid sample and the nucleic acid control are labeled with labels that are distinguishable from each other (e.g. different color fluorescent labels). The binding of the labeled probes, at any location on the chromosome, may be independently quantified and the ratio of binding of the nucleic acid sample to the nucleic acid control at any particular chromosomal location (i.e. DAPI band) may be calculated. Where there is no deletion or amplification the ratio will be about one. Where the nucleic acid sample contains an amplification the ratio of binding of nucleic acid sample to nucleic acid control will be greater than one. Conversely, where the nucleic acid sample contains a deletion, the ratio will be less than one.

Comparative genomic hybridization does not require hybridization against a metaphase chromosome. Alternatively, arrays of one or more nucleic acids each of which correspond to a nucleic acid found in a particular region of the chromosome may also serve as hybridization targets. In particular, high density arrays of nucleic acids attached to a solid support (e.g. a glass slide) in which each nucleic acid corresponds to a nucleic acid found in one of the glioma-associated amplifications or deletions provide a particularly effective CGH target for screening for glioma-associated sequences. Means of immobilizing nucleic acids or arrays of nucleic acids are well known to those of skill in the art.

Nucleic acids may be immobilized to solid supports or to linkers attached to solid supports through covalent bonds formed between the solid support and the 3' or 5' hydroxyl groups of the nucleic acid. Alternatively, the nucleic acids may be joined through introduced functional groups. Methods for immobilizing nucleic acids by introduction of various functional groups to the molecules are well known to those of skill in the art (see, e.g., Bischoff et al., *Anal. Biochem.* 164:336–344 (1987); Kremsky et al., *Nuc. Acids Res.* 15:2891–2910 (1987) which are incorporated herein by reference). For example, modified nucleotides can be incorporated into the nucleic acid PCR primers containing the modified nucleotide, or by enzymatic end labeling with modified nucleotides. Where the immobilized nucleic acids are relatively short (i.e., less than 200 nucleotides), the nucleic acids may be chemically synthesized directly on the solid support (see, e.g., Fodor et al. *Science,* 251: 767–773 (1991) and U.S. Pat. No. 5,143,854).

Suitable linkers attaching nucleic acids to solid supports are also well known. Generally linkers are either hetero- or homo-bifunctional molecules that contain two or more reactive sites that may each form a covalent bond with the respective binding partner (the solid support or the nucleic acid). For example, biological binding partners may be joined by a peptide linker, by a straight or branched chain carbon chain linker, or by a heterocyclic carbon. Heterobifunctional cross linking reagents such as active esters of N-ethylmaleimide have been widely used. See, for example, Lerner et al. *Proc. Nat. Acad. Sci. (USA),* 78: 3403–3407 (1981) and Kitagawa et al. *J. Biochem.,* 79: 233–236 (1976), which are incorporated herein by reference.

Methods of comparative genomic hybridization are well known to those of skill in the art. The use of CGH to detect the glioma-associated amplifications and deletions of the present invention is detailed in Example 1 and 2. In addition, methods of CGH are described in detail in Kallioniemi, et al. *Science,* 258: 818–821 (1992), Kallioniemi et al. *Proc. Natl. Acad. Sci. USA,* 91: 2156–2160 (1994), and in PCT Application No. WO 93-18186, which are incorporated herein by reference.

Detection by Amplification

Glioma-associated amplifications and deletions may also be detected by amplification methods. Typically, these methods involve amplifying a nucleic acid sequence found within an amplification or deletion region and detecting or quantifying the amplification product. Deletions may also be detected by amplifying flanking sequences on one or both sides of the deletion such that the amplified nucleic acid includes a deletion junction (the transition between the deleted and non-deleted region). When the amplification include flanking sequences on both sides of the deletion, presence of an amplification product indicates presence of the deletion.

The amplification may be by any of a number of means known to those of skill. These include polymerase chain reaction, quantitative polymerase chain reaction, ligase chain reaction, self-sustained sequence replication, and the like, as described above.

The amplification product may be detected by a variety of means well known to those of skill in the art. For example, the amplification product by be detected simply by size fractionating the reaction products (e.g. electrophoretically) and staining (e.g. with ethidium bromide) and directly visualizing the amplified DNA. Where the amplification primers or the constituent nucleotides themselves incorporate a label, the amplified product may be detected simply by detecting the incorporated label. Alternatively, the amplification product may be detected by hybridization with a probe specific to the amplification product as explained above in the description of Southern hybridizations.

One of skill in the art will appreciate that the foregoing methods of detection of genomic deletions are merely exemplary and there exist numerous other routine methods of detecting genomic deletions and amplifications.

Preparation of Probes to for CGH Detection of Glioma-Associated Amplifications and Deletions In a preferred embodiment, comparative genomic hybridization is performed using total genomic DNA probes. Both the nucleic acid sample that is to be tested (e.g. DNA from cells that may be from a glioma) and the nucleic acid control (genomic DNA from healthy cells) are prepared in a similar manner. Typically total genomic DNA is isolated from the respective sample cells or healthy control cells according to standard methods. The isolated probes are then digested to a characteristic length using a nuclease. Finally, each probe is labeled, typically by nick translation. For protocols detailing probe preparation and labeling see, for example, Sambrook, et al., *Molecular Cloning: A Laboratory Manual* 2nd ed., Vols. 1–3, Cold Spring Harbor Laboratory (1989), *Methods in Enzymology,* Vol. 152: *Guide to Molecular Cloning Techniques* (Berger and Kimmel (eds.), San Diego: Academic Press, Inc. (1987)), or *Current Protocols in Molecular Biology,* (Ausubel, et al. (eds.), Greene Publishing and Wiley-Interscience, New York (1987), all of which are incorporated herein by reference).

Preparation of Probes to Detect Particular Nucleic Acid Sequences Within Amplifications or Deletions In a preferred embodiment, the glioma-associated amplifications and deletions will be detected using nucleic acid probes that specifically hybridize with nucleic acid sequences located within the amplified or deleted region. One of skill in the art will appreciate that a deletion may also be detected using a probe that incorporates the nucleic acid sequences flanking a deletion and therefore spans the deletion when the deletion is present. Particularly preferred probes bind to a promoter, an open reading frame, or a gene within the deleted or amplified region. An open reading frame refers to a contiguous nucleic acid sequence that is transcribed (and hence codes for a polypeptide or protein or fragment thereof) and that lacks a stop codon.

Once an amplified or deleted genomic region has been identified, probes that specifically bind to nucleic acid sequences within that amplification or deletion may be prepared according to routine methods well known to those of skill in the art. The region may be sequenced by digesting chromosomal DNA with restriction enzymes and identifying nucleic acid fragments that are found within the deleted and amplified regions of the present invention using hybridization probes derived from genomic libraries spanning the particular chromosome of interest. The positive clones may then be subcloned into appropriate vectors and sequenced to determine the sequence of the corresponding deleted or amplified regions.

Genomic probe libraries spanning particular chromosomes at high resolution may be prepared using routine methods well known to those of skill in the art. Selected chromosomes are isolated by flow cytometry from cells blocked in metaphase, e.g., by the addition of colcemid, and stained with two DNA-binding fluorescent dyes. The stained chromosomes are then passed through a cell sorter and isolated (see, e.g., Blennow et al., *Hum. Genet.* 90:371–374 (1992). The isolated chromosome (e.g., chromosome 7) is then digested with restriction enzymes appropriate to yield DNA sequences of at least about 20 kb and more preferably about 40 kb. Techniques of partial sequence digestion are well known in the art. See, for example Perbal, *A Practical Guide to Molecular Cloning* 2nd Ed., Wiley N.Y. (1988). The resulting sequences are ligated with a vector which contains a resistance marker. The vector is transfected into and propagated in the appropriate host. Exemplary vectors suitable for this purpose include cosmids, yeast artificial chromosomes (YACs), bacterial artificial chromosomes (BACs) and P1 phage. Typically, cosmid libraries are prepared consisting of single clones of the transfected bacteria.

While it is possible to generate cosmid libraries, as described above, libraries spanning entire chromosomes are also available commercially (Clonetech, South San Francisco, Calif.) or from the Los Alamos National Laboratory.

The chromosome specific library of probes may be hybridized to the particular chromosome to determine which probes map (bind) at, or close to, the regions of interest. For example, Lichter et al., *Science,* 247:64–69 (1990), describe a method of mapping probes by FISH to metaphase chromosome spreads from normal cells using e.g., FITC as the fluorophore. The chromosomes may be visualized when they are counterstained by a general stain which stains DNA irrespective of base composition (e.g., GIEMSA, propidium iodide, or DAPI). The stained metaphases are visualized in a fluorescence microscope with a polychromatic beam-splitter to avoid color-dependent image shifts. The different color images are acquired with a CCD camera and the digitized images are stored in a computer. The hybridization pattern of the probes may be related to known chromosomal bands (See. Francke, U. *Cytogen. and Cell Gen.,* 65: 206–218 (1994)) yielding positional information.

Alternatively, a computer program may be used to calculate the chromosome axis for each chromosome, overlay the two (for single copy sequences) FITC signals perpendicularly onto this axis, and calculate the average fractional length (FL) from a defined position, typically the p-telomere. When the p-telomere is used as the reference point the position of each clone is expressed in units called "FLpter".

Other methods may be utilized alone or in conjunction with the above-described process to determine the sequence of nucleic acids from particular deletions or amplifications. For example, overlapping sequences in a large number of randomly selected cosmid clones can be identified by unique restriction enzyme "fingerprinting" and then assembled into overlapping sets of clones. Such techniques have been used to map various nonhuman genomes (see, e.g., Olson et al., *Proc. Natl. Acad. Sci. USA* 83:7826 (1986) and Coulson et al., *Proc. Natl. Acad. Sci. USA* 83:7821 (1986) which are incorporated herein by reference).

In addition, overlapping clones can be identified by hybridization with RNA probes. Cloning vectors are now available in which the promoters for two different polymerases, lie adjacent to a cloning site. Transcription with the corresponding available polymerases enables one to produce large quantities of RNA probes which correspond to either the coding or the non-coding strands (see, e.g. Wahl et al., *Methods in Enzymology* 152:572 (1987) and U.S. Pat. No. 5,219,726 which are incorporated herein by reference).

Finally, such mapping efforts may not be necessary to determine the sequences of the amplified and deleted regions. Genomic databases that containing the majority and soon perhaps all cDNA sequences in the human genome are available from commercial suppliers such as Human Genome Sciences Inc. (HGS, of Rockville Md., USA). In addition non-profit genomic databases are available to the public such as GenBank and a cDNA database prepared by DuPont Inc. (Wilmington, Del., USA).

Probe Labeling

The nucleic acid probes used to detect the genomic amplifications and deletions of the present invention are preferably labeled for use in in situ hybridization. The probes may be detectably labeled prior to the hybridization reaction. Alternatively, a directly detectable label which binds to the hybridization product may be used. Such a detectable label can be any material having a detectable physical or chemical property and have been well-developed in the field of immunoassays. Thus a label is any composition detectable by spectroscopic, photochemical, biochemical, immunochemical, or chemical means. Useful labels in the present invention include radioactive labels (e.g. $^{32}P$, $^{125}I$, $^{14}C$, $^{3}H$, and $^{35}S$), fluorescent dyes (e.g. fluorescein, rhodamine, Texas Red, etc.), electron-dense reagents (e.g. gold), enzymes (as commonly used in an ELISA), and the like. Examples of labels which are not directly detected but are detected through the use of directly detectable label include biotin and dioxigenin as well as haptens and proteins for which labeled antisera or monoclonal antibodies are available.

The particular label used is not critical to the present invention, so long as it does not interfere with the in situ hybridization of the probe. However, CGH using probes directly labeled with fluorescent labels (e.g. fluorescein-12-dUTP, Texas Red-5-dUTP, etc.) provided superior detection with reduced artifacts such as false positives. Thus direct-labeled probes are generally preferred.

A direct labeled probe, as used herein, is a probe to which a detectable label is attached. Because the direct label is already attached to the probe, no subsequent steps are required to associate the probe with the detectable label. In contrast, an indirect labeled probe is one which bears a moiety to which a detectable label is subsequently bound, typically after the probe is hybridized with the target nucleic acid.

In addition the label must be detectible in as low copy number as possible thereby maximizing the sensitivity of the assay and yet be detectible above any background signal. Finally, a label must be chosen that provides a highly localized signal thereby providing a high degree of spatial resolution when physically mapping the probe against the chromosome. Particularly preferred fluorescent labels include fluorescein-12-dUTP and Texas Red-5-dUTP.

The labels may be coupled to the probes in a variety of means known to those of skill in the art. In a preferred embodiment the probe will be labeled using nick translation or random primer extension (Rigby, et al. *J. Mol. Biol.*, 113: 237 (1977) or Sambrook, et al., *Molecular Cloning—A Laboratory Manual*, Cold Spring Harbor Laboratory, Cold Spring Harbor, N.Y. (1985)).

Nucleic Acid Sample Preparation

The FISH methods for detecting chromosomal amplifications and deletions associated with gliomas described herein can be performed on nanogram quantities of the subject nucleic acids. Paraffin embedded tumor sections can be used, as can fresh or frozen material. Because FISH can be applied to very small quantities of biological material, a number of types of samples can be used. For instance, small biopsy tissue samples from tumors can be used for touch preparations (see, e.g., Kallioniemi et al., (1992) supra.). Small numbers of cells obtained from aspiration biopsy or cells in bodily fluids (e.g., blood, urine, sputum and the like) can also be analyzed.

Kits for the Detection and Diagnosis of Gliomas

The present invention additionally provides for kits for the detection and diagnosis of gliomas. The kits include one or more probes that specifically bind to nucleic acid sequences located in the glioma-associated deletions and amplifications identified herein. In a particularly preferred embodiment, the kits include probes that specifically bind to promoters, genes, or open reading frames of nucleic acid sequences located within the deletion or amplification regions. The kits may also include instructional materials describing how to use the kit contents in detecting an amplification or a deletion associated with neoplastic growth of glial cells. In addition the kits may include one or more of the following: various labels or labeling agents to facilitate the detection of the probes, reagents for the hybridization including buffers, a metaphase spread, human Cot-1 DNA, bovine serum albumin (BSA) and other blocking agents, sampling devices including fine needles, swabs, aspirators and the like, positive and negative hybridization controls and so forth. Kits of similar makeup, but comprising probes specific to different chromosomal regions, are commercially available (see, e.g. Oncor Inc., Gaithersburg, Md., USA; Amersham Internat. PLC, Little Chalfont, Bucks, UK; and Vysis Inc., Naperville, Ill., USA).

EXAMPLES

The following examples are offered to illustrate, but not to limit the claimed invention.

Example 1

Detection of Glioma Associated Amplifications and Deletions by CGH Using Indirect-Labeled Probes DNA preparation and labeling Thirty specimens of glioblastoma multiforme (GBM), 20 primary and 10 recurrent, were obtained from the Tissue Bank of the Brain Tumor Research Center at the University of California, San Francisco (UCSF). The 10 recurrent tumors were from patients initially diagnosed with GBM. All specimens were frozen in liquid nitrogen immediately after resection and stored at $-80°$ C. Tumors were graded by the Division of Neuropathology at UCSF, where the presence of tumor in 15 of the 30 samples used for CGH analysis was examined and confirmed by frozen section. There was insufficient tumor tissue to do this in the other 15 samples.

Nine established glioma cell lines (Collins, *Int. Rev. Exp. Pathol.*, 24, 135–202 (1983); Rutka et al.,*Acta Neuropathol. (Berl.)*, 75, 92–103 (1987)) were obtained from the Brain Tumor Research Center (see Table 2). These cells were cultured in Eagle's minimum essential medium or Earle's balanced salt solution, each supplemented with 10% fetal calf serum.

TABLE 2

Chromosomal abnormalities noted in glioma cell lines.

Cell lines derived from glioblastoma multiforme:

| | |
|---|---|
| SF-126 | +(5)(p), +(7), −(13), +(20)(q13) |
| SF-188 | +(1q, +(2q)(21–32), −(6)(q16–23), +(7)(q22–32), +(7)(q21.1–21.3), +(8)(q22–24.2), −(10)(q), −(13), −(17)(q), +(20)(p, +(X), −(Y) |
| SF-295 | −(4q32–35), +(5), +(7), −(10), −(11)p, −(14), +(17)(q) |
| U-251 | +(3q)(22–29), +(7)(p), −(10)(p), −(13), +(15), −(18)(q), +(X), −(Y) |
| U-343 | −(6)(q), +(7), −(10), −(14), −(15), −(18)(q), +(Y) |
| A-172 | −(3)(p), −(4), −(11)q, −(12)p, −(13), −(14), +(X)(p), −(X)(q), −(Y) |

Cell lines derived from anaplastic astrocytoma:

| | |
|---|---|
| SF-268 | −(5)(q13–22), +(7)(q21–32), −(8)(p), −(10), +(11)(p), +(11)(q21–23), −(13)(q21–32), +(20)(p) |
| SF-763 | +(1)(q), +(3)(q22–29), −(4), +(5)(p), −(8)(p), +(8)(q22–24.3), −(9)(p), −(10)(p), +(11)(p11–12), +(13)(q), −(X) |
| SF-767 | −(1)(q), −(3)(p), +3(q), −(5)(p), −(5)(q14–31), −(6)(p), +(8)(q22–24.9), +(9), −(10), +(14)(q11.2–22) |

Chromosome amplifications and deletions are designated using standard banding pattern terminology. A "+" indicates an amplification while a "−" indicates a deletion. The first number in brackets (e.g. "(1)") represents the chromosome. The second bracket indicates the location on the chromosome of the deletion or amplification. Where there is no second bracket, the entire chromosome is deleted. P and q represent the p and q arm of the chromosome respectively, while the numbers in the second pair of brackets indicate the location of the deletion or amplification in terms of chromosomal bands. The presence of just a "p" or a "q" in the second pair of brackets indicates loss or amplification of the entire p or q arm.

Reference DNA was prepared from male and female buffy coat cells (mononuclear cells) from normal donors. Normal mononuclear and tumor cells were treated in a buffer of 0.1 mg/ml proteinase K, 0.5% sodium dodecyl sulfate, and 25 mM EDTA for 12 hr at 50° C. DNA was extracted with phenol/chloroform/isoamyl alcohol (25:24:1), and precipitated in 100% ethanol/7.5 M ammonium acetate. DNA concentration was quantitated and the purity verified by measuring absorbance at 260 nm and 280 nm.

Probes were prepared by nick translation using the Bio Nick labeling kit (Gibco, Bethesda, Md., USA). Total tumor DNA was digested by DNase I and labeled using DNA polymerase I, dCTP, dGTP, dTTP and biotin-14-dATP for 1 hr at 15C. DNase I concentration (0.0075 to 0.0225 units/$\mu$g DNA) was modulated to produce probe fragments 500 to 2500 base pairs long as determined by nondenaturing agarose gel electrophoresis.

Total mononuclear DNA was labeled under identical conditions as tumor DNA, except that digoxigenin-11-dUTP was substituted for dTTP and unlabeled dATP for biotinylated dATP.

DNA Hybridization

Target lymphocyte metaphase spreads were prepared from normal male lymphocytes using standard procedures. Metaphase chromosomes were denatured in 70% formamide and 2× SSC (0.3 M NaCl, 0.03 M sodium citrate, pH7) for 10 min at 85° C., dehydrated in a sequence of 70%, 85%, and 100% ethanol, air-dried and warmed to 37° C. on a slide warmer. Two hundred forty nanograms of labeled tumor and control DNA (matched for sex), and 20 $\mu$g of human Cot-1 DNA (Gibco) were precipitated in ethanol and dissolved in 50% formamide, 10% dextran sulfate, and 2× SSC. The probe mixture was denatured for 10 min at 85° C. and hybridized to the normal metaphase spread for 48 hr at 37° C.

Immunocytochemical staining

Slides were washed three times in 50% formamide/2× SSC, pH7, twice in 2× SSC and once in 0.1× SSC, each time for 10 min at 45° C. A final wash in 4× SSC at room temperature was followed by a 5 min pre-block with 4× SSC containing 1% bovine serum albumin. Bound DNA was stained for 30 min with 5 $\mu$/ml fluorescein isothiocyanate-avidin (Vector Laboratories, Burlingame, Calif.) and 2 $\mu$g/ml anti-digoxigenin Rhodamine (Boehringer Mannheim, Indianapolis, Ind.), washed with 4× SSC, 4× SSC with 0.1% triton, and 4× SSC, each for 10 min at room temperature, and counterstained with 0.4 $\mu$M 4,5-diamino-2-phenylindole (DAPI) in an antifade solution.

Image analysis

Green, red, and blue fluorescence images were separately acquired and analyzed using a semiautomated Quantitative Image Processing System that is based on the Zeiss fluorescence microscope, a triple-band pass filter (Chroma Technology, Brattleboro, Vt., USA), an NA1.4, 63x objective, and a Photometrics CH25D camera (Photometrics Ltd., Tucson, Ariz., USA) interfaced to a SUN 4/330 work station (SUN Microsystems, Inc., Mountain View, Calif., USA). The analysis of acquired images was controlled by the SCIL-image software package (Delft Centre for Image Processing, Delft, Netherlands) (Kallioniemi et al., (1992) supra.).

Profiles of fluorescence intensity along chromosomes were computed and normalized using the XWHOOLZ program (Medical Research Council, Edinburgh, Scotland). This program plots the fluorescence ratio (green versus red) as a function of chromosome length. The ratio is normalized to equalize total green and red fluorescence intensity for the entire image. A green/red ratio of 1.0 is taken to indicate similar relative copy number for the tumor and reference probes. A ratio greater than 1.0 reflects relatively greater binding by the tumor DNA, indicating increased copy number of that locus. A ratio less than 1.0 indicates decreased copy number at that locus. Individual chromosomes were identified using the DAPI-banded image. The ratio profiles for all 46 chromosomes were calculated by the XWHOOLZ program.

For each tumor or cell line, at least two complete metaphase spreads were analyzed, yielding four ratio profiles for each autosomal chromosome and two for each sex chromosome. Ratio changes of 0.25 or more (either above or below the baseline of 1), with standard deviations less than 0.20 were defined as indicative of changes in DNA copy number. Ratio changes at the centromeres or P-arms of acrocentric chromosomes were not interpreted because these regions were blocked with Cot-1 DNA, resulting in very low-signal intensities.

Results

The ratio profile for chromosome 10 showed the loss of a whole chromosome, and that for chromosome 13 showed an interstitial deletion on the q arm. The ratio profile for chromosome 11 showed the gain of a whole p arm and an interstitial gain (an "amplification") on the q arm. The ratio profile for chromosome 7 showed a gain of the whole chromosome and the suggestion of a separate peak at 7p11.2, which could represent a separate region of amplification. A loss of chromosome 10 involving the whole p and q arms was observed with a superimposed amplification on the q arm.

A control experiment was performed comparing normal male DNA to normal male DNA. As expected, most of the autosomal chromosomes showed a copy number ratio of 1.0. However, there was an apparent loss on chromosome 19, where the ratio was less than 1.0.

In order to evaluate the prevalence and position of these apparent losses in hybridizations comparing normal DNAs, 10 control experiments were performed in which normal male DNA labeled with biotin was hybridized to normal female DNA labeled with digoximgenin. Fluctuations from the baseline always appeared as deletions and were consistently found in five regions: 1p (5 cases), 16p (4 cases), 19 (6 cases), and 22 (4 cases). For this reason, ratio changes were not interpreted as copy number alterations at these loci.

Chromosomal abnormalities noted in nine cell lines are shown in Table 2. Frequent aberrations were defined as those present in more than 25% of cases. The most frequent changes were gains involving chromosome 7 (6 cell lines), and losses involving chromosomes 10 (8 cell lines) and 13 (5 cell lines). Other frequent changes were losses on chromosomes 4, 14, and Y (3 cell lines each), and gains on chromosomes 3q (3 cell lines), 5p (4 cell lines), 8q (3 cell lines), and Xp (3 cell lines). Although most of the abnormalities involved whole arms or whole chromosomes, some were interstitial gains and losses. On chromosome 8, three cell lines were amplified at (8)(q22–24.2), a location that is consistent with the c-myc oncogene. These results confirm a previously reported c-myc amplification in one of these cell lines, SF-188 (Trent et al., Proc. Natl. Acad. Sci. USA, 83, 470–473 (1986))), however, this amplification has not previously been reported in the other cell lines.

Other novel amplifications and deletions were detected as well. Two cell lines had interstitial gains on 7q: SF-188 had amplifications involving (7)(q21.1–21.3) and (7)(q22–32), and SF-268 had a gain of (7)(q21–32). Three cell lines had amplifications in (3)(q26.2–2-29), and individual cell lines had amplifications on (2)(q21–32), (11)(q11–12), (11)(q21–23), (14)(q11.2–22), and (20)(q13). Examples of interstitial deletions include the loss of (13)(q21–32) in SF-268, (5)(q13–22) in SF-268, and (5)(q14–31) in SF-767.

The most common gains and losses detected in the 20 primary GBM tumors included a gain of chromosome 7 (7 tumors), loss of (9)(p) (7 tumors), loss invoking chromosome 10 (9 tumors), loss involving chromosome 13 (5 tumors), and loss of Y (7 tumors). Eight tumors had loss of chromosome 10, and 1 had a deletion of (10)(q22–26). Two tumors had loss of chromosome 13, and 3 had interstitial deletions (on (13)(q13–21), (13)(q21–22), and (13)(q12–31). The common area of loss on chromosome 13 was (13)(q21).

Many of the copy number changes found in the 10 recurrent tumors occurred at the same loci as those in primary tumors. Three recurrent tumors had gains on chromosome 7, 4 had losses on 9p, 3 had losses on chromosome 10, 5 had losses on chromosome 13, and 3 lost chromosome Y. Two recurrent tumors had interstitial deletions of chromosome (10)(q22–26); three had interstitial deletions on chromosome 13 involving (13)(q14–21), (13)(q14–22), and (13)(q14–31). However, losses were found on chromosomes 6 and 14 that occurred more frequently in recurrent tumors than in primary tumors. These included three interstitial deletions on chromosome 6: (6)(q16–24), (6)(q13–27), and (6)(q23–27); one whole chromosome loss of 14; and two deletions of (14)(q22–32).

Example 2

Detection of Glioma Associated Amplifications and Deletions by CGH Using Direct-Labeled Probes DNA Extraction Ten established glial tumor cell lines (A172, SF126, SF188, SF268, SF295, SF763, SF767, U87MG, U251NCI, and U343MGA) were obtained from the tissue bank of the Brain Tumor Research Center, University of California, San Francisco (Table 3).

TABLE 3

List of Cell Lines

| Cell line | Diagnosis | Sex | Passage no. |
| --- | --- | --- | --- |
| A172 | GBM | Male | 33 |
| SF126 | GBM | Female | 71 |
| SF188 | GBM | Male | 193 |
| SF268 | AA | Female | 27 |
| SF295 | GBM | Female | 32 |
| SF763 | RRAA | Female | 143 |
| SF767 | RRAA | Female | 147 |
| U87MG | GBM | Female | 222 |
| U251NCI | GBM | Male | 77 |
| U343MGA | GBM | Male | 455 |

GBM - glioblastoma multiforme; AA - anaplastic astrocytoma; RRAA - recurrent anaplastic astrocytoma.

The cells were cultured in Eagle's minimum essential medium with Earle's balanced salt solution supplemented with 10% fetal calf serum. Genomic DNA was extracted and purified from the cells according to methods described by Sambrook et al., supra. Reference DNA was prepared from leukocytes of normal male and female donors. DNA was quantitated with a fluorometer (model TKO 100, Hoefer Scientific Instruments, San Francisco, Calif., USA).

Metaphase Preparation

Metaphase spreads were prepared from phytohemagglutinin-stimulated peripheral blood lymphocytes of a normal healthy male donor according to standard procedures.

DNA Labeling and In Situ Hybridization

CGH was first performed by labeling normal DNA with fluorescein-12-dUTP and tumor DNA with Texas Red-5-dUTP (DuPont, Wilmington, Del., USA) by nick translation, according to protocols provided in the kit. To verify the alterations in copy number observed in the hybridizations, control experiments were performed in which the labels were reversed; Texas Red was incorporated into normal DNA and fluorescein into tumor DNA. One negative control (normal versus normal) and one positive control (600PE, a well-characterized breast cancer cell line) were included in each experiment to monitor hybridization quality.

The optimal size for double-stranded probe fragments ranged from 200–2000 bp. Slides containing metaphase chromosomes were denatured in 70% formamide and 2× SSC (0.3 M NaCl, 0.03 M sodium citrate, pH 7) for 5 min at 75° C. and denatured in a graded series of ethanols. The slides were air dried and warmed to 37° C. on a slide warmer. Two hundred nanograms of each labeled tumor and normal DNA and 20 μg of human Cot 1 DNA (BRL) were ethanol precipitated and redissolved in 10 ml of 50% formamide, 10% dextran sulfate, and 2× SSC (pH 7). The probe mixture was denatured for 5 min at 75° C. and hybridized to normal metaphase chromosomes for 48 hr at 37° C.

Slide Washing Protocol

Slides were washed at 45° C. three times in 50% formamide/2× SSC (pH 7), twice in 2× SSC, and once in 0.1× SSC for 10 min each and then at room temperature in 2× SSC and phosphate buffer with 0.1% NP-40 (pH 8) for 10 min each. They were then counterstained with 0.2 μM 4,6-diamino-2-phenylindole (DAPI) in an antifade solution. The slides were viewed under a Zeiss fluorescence microscope equipped with a double band pass filter (Chroma Technology, Brattleboro, Vt., USA) to visualize fluorescein and Texas Red signals simultaneously.

Image Analysis

Blue, green, and red images were acquired with a Quantitative Image Processing System, and ratio profiles of fluorescence and intensity along the chromosomes were generated (for detailed description, see Kallioniemi et al., (1992), supra.). For each sample, seven metaphase spreads were acquired. At least four complete spreads were analyzed, yielding eight ratio profiles for each autosome and four for each sex chromosome. Hybridization quality was determined by visual inspection of the images; only those with uniform hybridization were acquired and used for analysis.

Definition of CGH Ratio Thresholds

To define ratios that were indicative of changes in DNA copy number, 21 CGH experiments were performed using normal control DNA. The average ratio changes and standard deviations were calculated using standard algorithms. The average ratio for all 21 hybridizations was 0.99 (range, 0.9–1.1). The average standard deviation was 0.04 (range, 0.02–0.06). Taking these findings into consideration, upper and lower ratio thresholds of 1.2 and 0.8, respectively were chosen. Any change in ratio in excess of these thresholds was interpreted as indicative of DNA copy number changes only if found in both forward and reverse experiments. Amplifications were defined both by a ratio greater than 2.0 and by visual inspection.

Results

Exchange of Labels of Tumor and Reference (Control) DNA

As expected, the average green-to-red (copy) ratio for all the chromosomes was 1.0. The exchange of labels in tumor and reference (control) DNA had no effect on the observed copy ratio. This was exemplified by CGH analysis of one of the cell lines; U87MG. Each decrease in the ratio of green to red in a "forward" hybridization (tumor DNA labeled in green) was matched by an increase in the ratio of green to red in a "reverse" hybridization (tumor DNA labeled in red). For example, the loss of the short (p) arm of chromosome 6 and interstitial deletions on 6q12–14 and 6q23.1–24.1 in a "forward" hybridization, were confirmed by ratios greater than 1.0 at the same location in a "reverse" hybridization. The same result was observed at 7q32–36.

Chromosome Gains and Losses Detected in the Ten Cell Lines

Chromosomal aberrations detected by CGH in the ten cell lines are listed in Table 4. Losses, in order of frequency, were observed on chromosomes 10, 18, 13, 11, 9, 14, 4, 6, 1, and X. Chromosome 10 was lost in four cell lines; there was total or partial loss of the p arm in three cell lines and deletions on the q arm in two cell lines. Chromosome 18 was lost in three cell lines, and 18q was lost in six other cell lines. Chromosome 13 was lost in four cell lines, and four cell lines displayed an interstitial deletion on 13q. Chromosome arm 9p was lost in two cell lines, and terminal or interstitial deletion on 9p was observed in three others. Whole loss or partial deletion was frequently observed on 4q (seven cell lines), 11q (six cell lines), 14q (five cell lines), X (five cell lines), 1p (four cell lines), and 6q (three cell lines).

TABLE 4

Losses and gains detected by CGH in the 10 glioma cell lines listed in Table 3. − indicates loss, + indicates gain, ++ indicates amplification.

A172  −(1)(P22–34.4), −(1)(p33–pter), ++(1)(q22–24), −(3)(p12–13), +(3)(q21qter), −(4)(q13), ++(5)(q31.2–32), +(7)(q)11), −(8)(q12–13), −9p, +9q, −(10)(q25–26), −(11(q14–25), −(12)(p13), −13, 14, −(18)(q12.3–23), ++(19)(q13.4), −22, −(X)(q21–26), +(X)(p22.1–pter), +(X)(q27.2–qter), −Y TABLE 4-continued Losses and gains detected by CGH in the 10 glioma cell lines listed in Table 3. − indicates loss, + indicates gain, ++ indicates amplification.

SF126  ++(1)(p36.2–pter), +5p, −(5)(q11.2–23.2), +7p, −(9)(p21–pter), −10p, +)11)(q12–13), −(11)(q23), −13, −(18)(q21.3–qter), ++(20)(q13.1–qter)

SF188  −1p, +1q, −5, −(6)(q12–23.2), ++(8)(q24), +10p, −10q, −(11)(q12–22), −13, −14, +16, ++(17)(p11.2–12), −18, −19, +20, +X, +Y

SF268  −(2)(p24–pter), −(2)(q14.2–32.2), −(3)(p11.2–21.3), −3q, −4, −(5)(q11.2–23.2), −8p, −(8)(q11.2–23.2), −(9)(q21–pter), −10, +11p, ++(11)(q14–21), ++(11)(q23), −(13)(q31), −(14)(q11.2–24), ++(14)(q31–qter), −16, +(17)(q24–qter), −18q, +20q, −22, −X SF295  −(4)(q33–35), +7, −10, −11p, −(11)(q11.2–14), −14, −(15)(q11.2–22.2), +17q SF763  ++(1)(p12–22), −2q, −(3)(p12.2–23, +(3)(q11.2–12), +(3)(q23–qter), −4 +5p, −5q, −(7)(q22–qter), −8p, −(8)(q11.2–23), ++(8)(q24), −9p, −(9)(q13–22), −(10)(q14–pter), ++(11)(p11.2–12), −(11)(q23), −(12)(p11.2–12), +(12)(p13), −(12)(q12), −(13)(q12–13), ++(14)(q22–23), ++(17)(p11.2–12), −17q, −18, −(19)(p13.2–pter), ++(19)(q13.3–qter), +20q, −21, +(22)(11.2–12), −X SF767  −2q, −3p, +3q, −4, +5p, +5q, −6 +(7)(p11.2–21.2), −(7)(p21.2–pter), −(7)(q21–qter), −(8)(p11.2–22), +(8)(q11.2–21.2), ++(8)(q24), +9, −10 ++(10)(q22), −11, +12p, −(12)(q21–qter), −13, ++(14)(q11.2–13), +15, +16q, +17, −18, +19q, +20q, −Xp, −(X)(q11.2–26)

U87  ++(1)(p13), −(1)(p22), −6p, −(6)(q12–14), −(6)(q23.2–24.1), +(7)(q32–qter), +(9)(p12–13), −(9)(p21–22), +9q, −(11)(q14–qter), −(12)(q21–23), −(13)(q12), −(13)(q21), +(13)(q22–34), +(14)(q21.2–qter), −(16)(p13.2–pter), −18, −20p, +20q, −X U251  +1p, −(2)(q32.3–35), +(3)(q23–qter), (4)(q32–qter), −(7)(p21–pter), +9p, −10p, ++(10)(q26), −(13)(q31–34), ++(15)(q13), ++(15)(q15), +17p, −18q, +(X)(q21)

U343  −(1)(p31.3–32), −(1)(p34.3–35), −4, −6q, +7, −(8)(q24.2–qter), −10, −14, −18q, −22, +Y The most common gain occurred on chromosome 7. Gain of this whole chromosome was detected in two cell lines (SF295 and U343). Two cell lines (A172, SF767) had a gain of 7pter-q 11, and SF763 had a gain of 7p21.2-q 11. SF126 and U251 had a gain on 7p, and U87 had a gain on 7q32-qter. The other major gains were on 20q (five cell lines), 19q (three cell lines), and 5p (three cell lines).

Possible isochromosomes were detected for chromosome arms 1q (SF188), 5p (SF126, SF763, SF767), 10p (SF188), 3q (SF767), and 20q (U87MG). An isochromosome represents a type of rearrangement in which the breakpoints are at or close to the centromere and two of the same arms are separated by the centromere. Because CGH provides a relative gain or loss in the DNA sequence copy number, the ratio for an isochromosome should show a relative loss of one arm, complemented by a relative gain of the other.

Sites of DNA Amplification

Several sites of DNA amplification were detected in the cell lines. On chromosome 1, there was one such site on (1)(p36.2-pter) (SF126), a second on (1)(p13) (SF763 and U87), and a third on (1)(q22–24) (A172). Amplification of (8)(q24) was detected in three cell lines (SF188, SF763, and SF767). Amplifications were also detected on (10)(q22) in SF767 and on (10)(q26) in U251. A very large amplification displaying two amplicons was found on (11)(q14.3–24) in SF268. Two adjacent amplicons were also detected on (15)(q12–21) in U251. Three different amplification sites were detected on 14q: (14)(q11.2–13) in SF767, (14)(q22–23) in SF763, and (14)(q31-qter) in SF268. In addition to these, amplifications on (5)(q31.2) (SF172), (11)(p11.2–12) (SF763), (17)(p11.2–12) (SF188 and SF763), (19)(q13.4) (A172 and SF763), and (20)(q13.1–13.3) (SF126) were detected.

CGH using direct labeled probes as described herein demonstrates a more detailed picture of genetic aberrations in glioma cell lines than CGH performed using indirect-labeled probes as described in Example 1. For example, the protocol described in Example 1 revealed a deletion on 9p only in one cell line, while CGH using direct-labeled probes detected it in five. In addition, several small amplifications were identified using direct-labelled probes that were missed when using indirect-labeled probes.

Previous investigators have described artifacts in the CGH ratio on 1p, 16p, 17p, 19, and 22 (Kallioniemi et al. *Proc. Nat'l. Acad. Sci. USA*, 91:2156–2160 (1994)). In those studies, probes were labeled with digoxigenin and biotin and were visualized by immunostaining. The artifacts were due to preferential binding of the probe labeled with digoxigenin over the probe labeled with biotin. The improved protocols provided herein, by using nucleotides labeled with fluorescein and Texas Red, reduced these artifacts. In addition, the elimination of antibody-conjugated fluorochromes produced smooth hybridizations, making ratio profiles easier to interpret.

The above description is illustrative and not restrictive. Many variations of the invention will be apparent to those of skill in the art upon review of this disclosure. Merely by way of example, while detection of glioma-associated amplifications and deletions is illustrated with CGH, the invention is not so limited. The scope of the invention should therefore be determined not with reference to the above description, but instead should be determined with reference to the claims along with their full scope of equivalents.

What is claimed is:

1. A labeled probe that specifically hybridizes to a polynucleotide sequence on a human chromosome under stringent conditions, said polynucleotide sequence being located in a chromosomal region selected from the group consisting of (1)(p34.2–34.3), (5)(q31.2), (19)(q13.4), and (20)(p1.2).

2. The probe of claim 1, wherein said probe has greater than 95% sequence identity to a nucleic acid sequence found in a chromosomal region selected from the group consisting of (1)(p34.2–34.3), (5)(q31.2), (19)(q 13.4), and (20)(p11.2).

3. The probe of claim 1, wherein the probe consists of an open reading frame of a nucleic acid found within a chromosomal region selected from the group consisting of (1)(p34.2–34.3), (5)(q31.2), (19)(q13.4), and (20)(p11.2).

4. The probe of claim 1, wherein said probe is a nucleic acid from a chromosomal region selected from the group consisting of (1)(p34.2–34.3), (5)(q31.2), (19)(q13.4), and (20)(p11.2).

5. The probe of claim 1, wherein the probe is fluorescently labeled.

6. The probe of claim 1, wherein the probe is directly labeled with a fluorescent label.

7. A kit for the detection of deletions or amplifications associated with neoplastic growth of a glioma, the kit comprising a compartment which contains a nucleic acid probe which specifically hybridizes to a polynucleotide found in a chromosomal region selected from the group consisting of (1)(p34.2–34.3), (5)(q31.2), (19)(q13.4), and (20)(p11.2).

8. The kit of claim 7, wherein the probe is labeled.

9. The kit of claim 8, wherein the probe is directly labeled with a fluorescent label.

10. The probe of claim 1, wherein said probe is immobilized on a solid support.

11. The probe of claim 10, wherein said probe is a probe in an array of two or more different probes.

12. The probe of claim 11, wherein said array comprises two or more probes that specifically hybridize to a polynucleotide sequence on a human chromosome under stringent conditions, said polynucleotide sequence being located in a chromosomal region selected from the group consisting of (1)(p34.2–34.3), (5)(q31.2), (19)(q13.4), and (20)(p11.2).

13. The kit of claim 7, wherein said probe is immobilized on a solid support.

14. The kit of claim 13, wherein said probe is a probe in an array of two or more probes.

15. The kit of claim 14, wherein said array comprises two or more labeled probes that specifically hybridize to a polynucleotide sequence on a human chromosome under stringent conditions, said polynucleotide sequence being located in a chromosomal region selected from the group consisting of (1)(p34.2–34.3), (5)(q31.2), (19)(q13.4), and (20)(p11.2).

16. The probe of claim 4, wherein said probe is a nucleic acid from chromosomal region (1)(p34.2–34.3).

17. The probe of claim 4, wherein said probe is a nucleic acid from chromosomal region (5)(q31.2).

18. The probe of claim 4, wherein said probe is a nucleic acid from chromosomal region (19)(q13.4).

19. The probe of claim 4, wherein said probe is a nucleic acid from chromosomal region (20)(p11.2).

20. The kit of claim 7, wherein the probe consists of an open reading frame of a nucleic acid found within a chromosomal region selected from the group consisting of (1)(p34.2–34.3), (5)(q31.2), (19)(q13.4), and (20)(p11.2).

21. The kit of claim 7, wherein said probe is a nucleic acid from a chromosomal region selected from the group consisting of (1)(p34.2–34.3), (5)(q31.2), (19)(q13.4), and (20) (p11.2).

22. The kit of claim 21, wherein said probe is a nucleic acid from chromosomal region (1)(p34.2–34.3).

23. The kit of claim 21, wherein said probe is a nucleic acid from chromosomal region (5)(q31.2).

24. The kit of claim 21, wherein said probe is a nucleic acid from chromosomal region (19)(q13.4).

25. The kit of claim 21, wherein said probe is a nucleic acid from chromosomal region (20)(p11.2).

* * * * *